United States Patent [19]

Eldridge, Jr.

[11] Patent Number: 4,591,048
[45] Date of Patent: May 27, 1986

[54] DISPOSABLE COLLECTOR FOR SURGICAL IMPLEMENTS

[75] Inventor: John D. Eldridge, Jr., Newport Beach, Calif.

[73] Assignee: American Hospital Supply Corp., Evanston, Ill.

[21] Appl. No.: 696,146

[22] Filed: Jan. 29, 1985

Related U.S. Application Data

[63] Continuation of Ser. No. 374,789, May 4, 1982, abandoned, which is a continuation-in-part of Ser. No. 16,971, Mar. 2, 1979, abandoned.

[51] Int. Cl.$^4$ ............................................. A61L 17/02
[52] U.S. Cl. .................................... 206/63.3; 206/382
[58] Field of Search .................. 206/63.3, 382, 383, 206/380, 460, 818, 359, 223

[56] References Cited

U.S. PATENT DOCUMENTS

| | | | |
|---|---|---|---|
| 670,096 | 3/1901 | Brabant | 206/382 |
| 2,771,990 | 11/1956 | Buschkamper | 206/382 |
| 4,008,802 | 2/1977 | Freitag | 206/382 |
| 4,167,230 | 9/1979 | Barratt | 206/63.3 |
| 4,243,140 | 1/1981 | Thrun | 206/63.3 |

FOREIGN PATENT DOCUMENTS 343410  1/1917  France ................. 206/382

Primary Examiner—Joseph Man-Fu Moy
Attorney, Agent, or Firm—Donald L. Barbeau

[57] ABSTRACT

A disposable collector for surgical implements which utilizes a pair of sponge plastic pads movable between a coplanar position to receive surgical implements, such as semicircular-shaped surgical needles and a folded position with their peripheral or frame portions in mutual contact to form an enclosure having depressed areas defining rows and columns of implement receiving elements, bordered by areas of depressions.

In one embodiment the implement receiving elements are completely surrounded by depressed portions; in another embodiment a pair of crescent-shaped depressed portions extend in opposite directions from the implement receiving elements.

12 Claims, 12 Drawing Figures

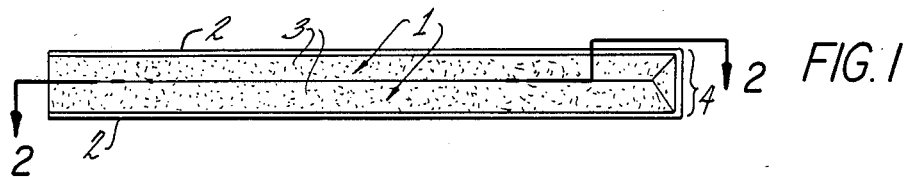
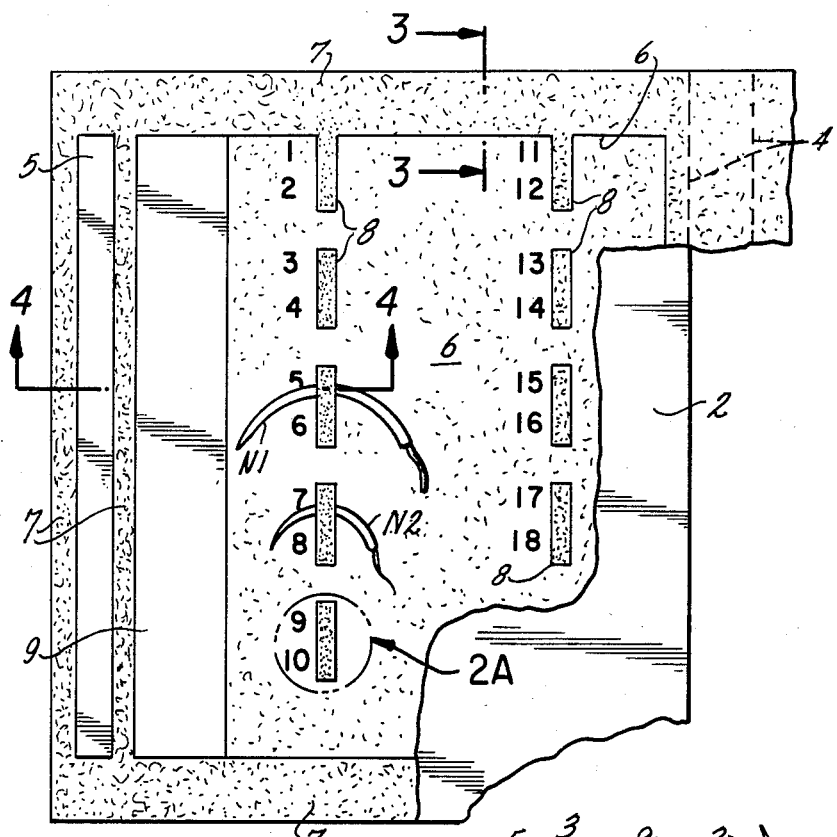
FIG. 1
FIG. 2
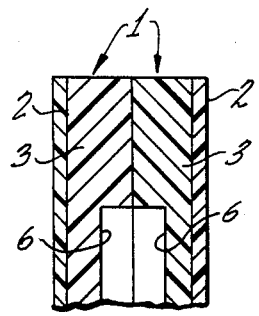
FIG. 3
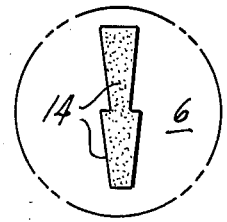
FIG. 2A
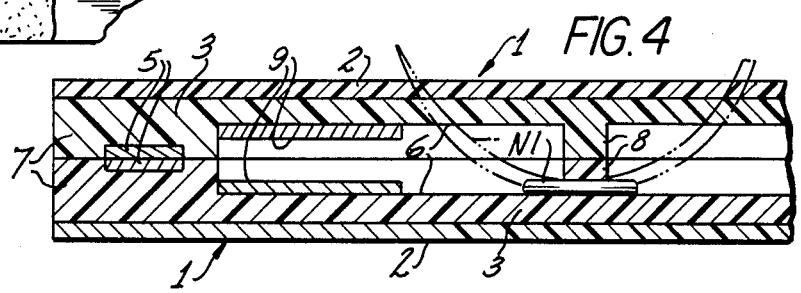
FIG. 4
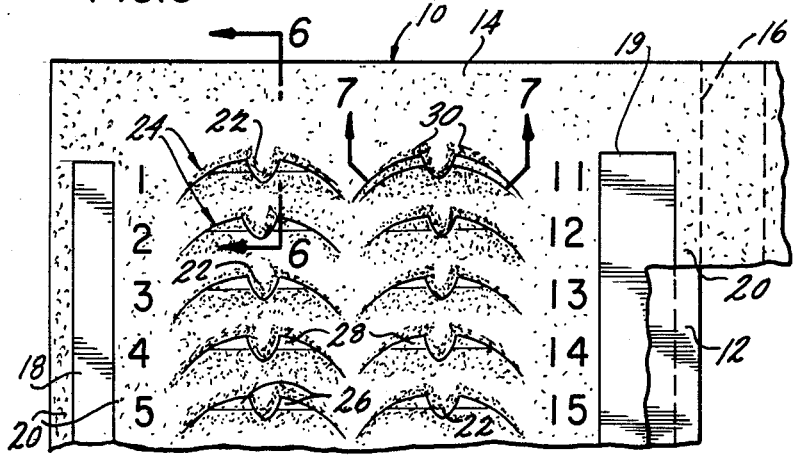
FIG. 5
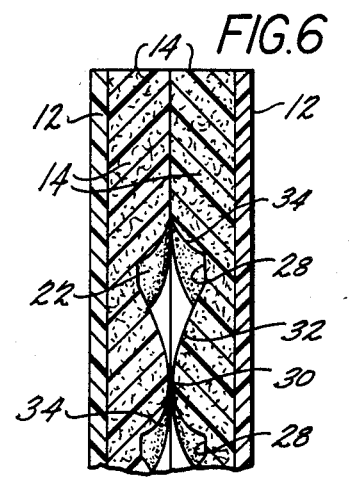
FIG. 6

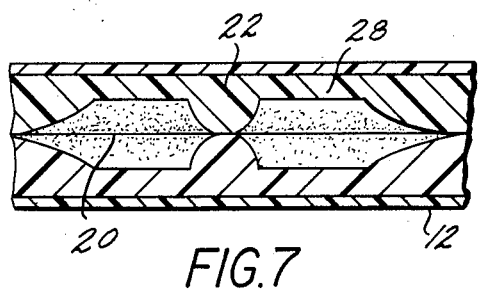
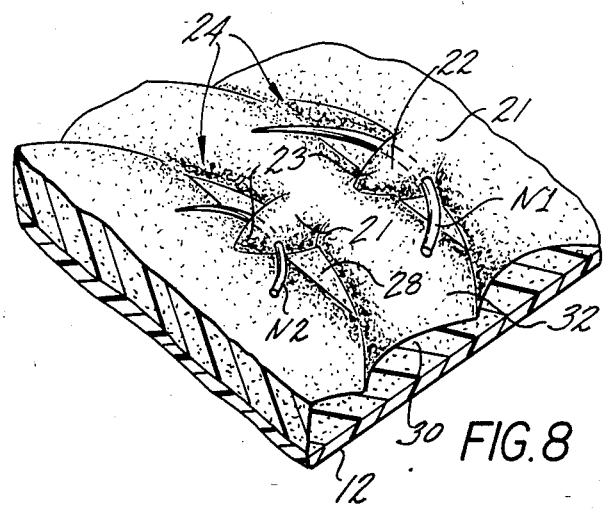
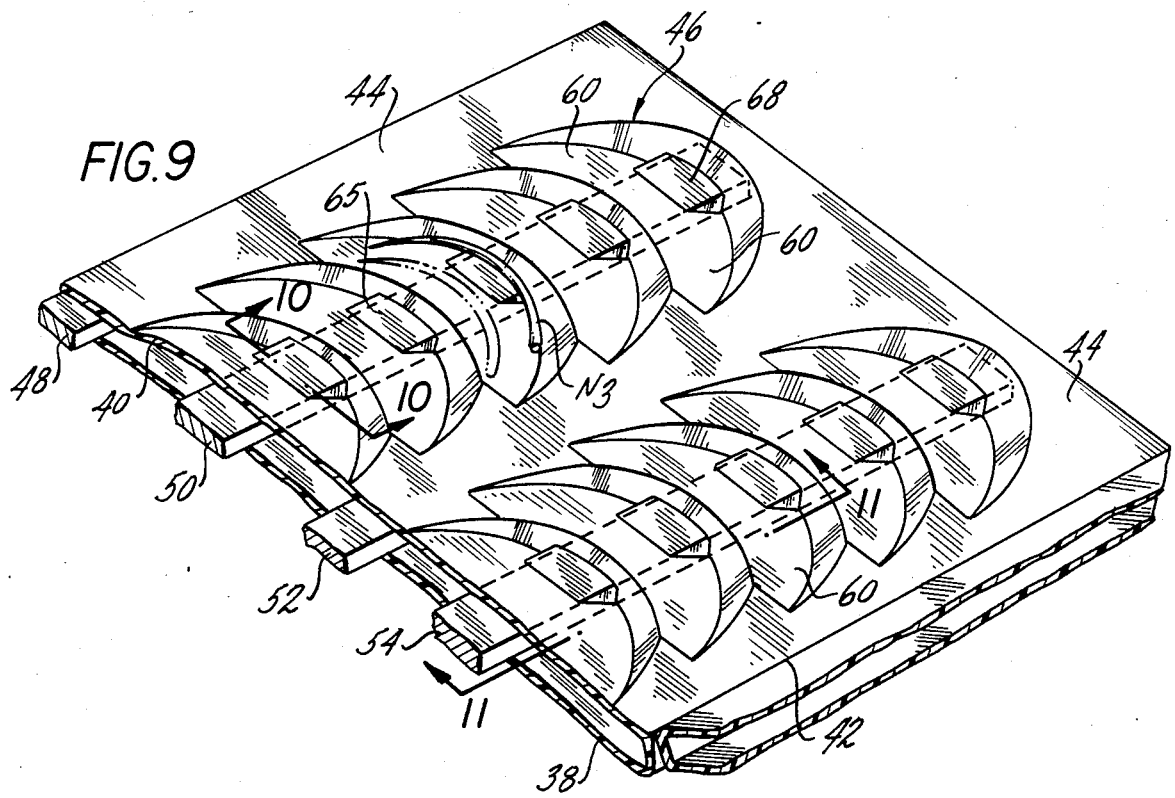
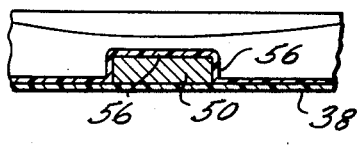
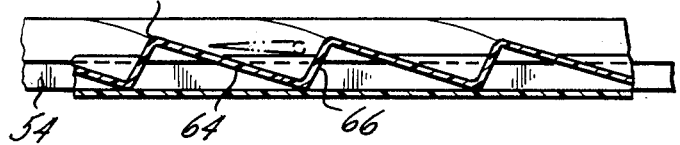

DISPOSABLE COLLECTOR FOR SURGICAL IMPLEMENTS

REFERENCE TO RELATED APPLICATIONS

This application is a continuation of application Ser. No. 374,789, filed May 4, 1982, now abandoned, which is a continuation-in-part of application Ser. No. 016,971, filed Mar. 2, 1979, now abandoned.

BACKGROUND OF THE INVENTION

In surgery, it is common practice to utilize a large number of small, expendable, surgical elements, principally semicircular needles, each being preattached to a surgical thread. As the number of implements is increased, the problem of accounting for every implement is increased. A further problem is to minimize the chance of injury or infection from accidental contact with the implements.

Examples of disposable collectors for surgical implements are shown in the following patents: 3,727,658, 3,944,069, 4,008,802, and in Application Ser. No. 006,732, filed Jan. 26, 1979, for DISPOSABLE SURGICAL NEEDLE COLLECTOR.

SUMMARY OF THE INVENTION

The present invention is directed to a solution of the problems indicated, and is summarized in the following objects:

First, to provide a disposable collector for surgical implements which is readily used, under the stress of surgery, to receive and retain for counting, a relatively large number of surgical implements.

Second, to provide a disposable collector which utilizes a pair of hinged pad units, each having rows and columns of implement receiving needles in a flat or nearly flat position, with respect to the pads, so that the pads, when folded, readily urge the implements toward a flat position.

Third, to provide a disposable collector for surgical implements, as indicated in the previous object, wherein the pads include peripheral portions surrounding the collected implements to effect complete closure of the implements.

Fourth, to provide a disposable collector for surgical implements, an embodiment of which utilizes implement receiving elements arranged in rows and columns, each element being entirely surrounded by a depressed area dimensioned to receive the entire surgical implement.

Fifth, to provide a disposable collector for surgical implements wherein the implement receiving elements are disposed in rows and columns and are particularly arranged to receive semicircular surgical needles by providing a pair of arcuate, laterally extending depressions for each needle.

BRIEF DESCRIPTION OF THE DRAWINGS

These as well as other features of the present invention will become more apparent upon reference to the drawings wherein:

FIG. 1 is an edge view of the disposable collector for surgical implements shown in its folded condition;

FIG. 2 is a plan view of one collector unit taken through 2—2 of FIG. 1 with a portion of the other collector unit shown fragmentarily in its folded state and a portion shown fragmentarily in its open or implement receiving state;

FIG. 2A is an enlarged fragmentary plan view corresponding to circle 2A of FIG. 2 showing a modified implement receiving embossment;

FIG. 3 is an enlarged fragmentary sectional view of the collector in its folded state taken through 3—3 of FIG. 2;

FIG. 4 is an enlarged fragmentary sectional view of the collector in its folded state taken through 4—4 of FIG. 2 and, indicated by dotted lines, a semicircular needle as it would appear if in a vertical position;

FIG. 5 is a plan view corresponding to FIG. 2 showing a second embodiment of the collector;

FIG. 6 is an enlarged fragmentary sectional view of the second embodiment of the collector shown in its folded state taken through 6—6 of FIG. 5;

FIG. 7 is an enlarged fragmentary sectional view of the second embodiment of the collector in its folded state, taken through 7—7 of FIG. 5;

FIG. 8 is a fragmentary perspective view of the second embodiment, showing two differently sized needles being retained;

FIG. 9 is a fragmentary perspective view of a third embodiment of the collector;

FIG. 10 is a sectional view of the third embodiment taken generally through 10—10 of FIG. 9; and FIG. 11 is a sectional view of the third embodiment taken through 11—11 of FIG. 10.

DETAILED DESCRIPTION OF THE PREFERRED EMBODIMENT

Referring to FIGS. 1 through 4, the disposable collector for surgical implements herein illustrated includes a pair of implement collector units 1, each having a backing plate 2. The plates 2, as shown, are of plastic, but may be of any relatively stiff material, such as cardboard. Each plate 2 is covered by a foamed plastic pad 3. The backing plates are joined together by a dual hinge 4 formed by weakening the backing plate along parallel lines.

The implement collector units 1 are preferably square or rectangular and the foamed plastic pads 3 receive magnet strips 5 disposed along the margin of each pad opposite from the dual hinges 4. The construction, as so far described, may be considered as conventional.

Each plastic pad 3 is provided with a depressed area 6 occupying a major portion of the plastic pad. Surrounding the depressed area 6 is a mutually engageable peripheral frame 7 are rows and columns of implement receiving embossments 8. The embossments extend the full thickness of the foamed plastic pads 3. Each embossment is relatively narrow and receives one or two, as illustrated, semicircular needles of larger or smaller dimension, as represented by N1 and N2 in FIG. 2.

The needles are inserted by a surgical pincer (not shown). In order to effect insertion, the needle is rotated about its center of the curvature or nearly so with the needle disposed at the base of the embossment 8, as indicated by dotted lines in FIG. 4. After insertion, the needle is pressed about the axis of its portion received in the embossment 8, causing the needle to assume a horizontal position, as represented in FIGS. 2 and 4.

Because of the narrow width of the embossments 8, the needles are easily turned to a position, essentially flat, with respect to the depressed area 6. In this regard, it should be noted that the needles tend to make apertures in the embossments which are arcuate with the result that if the embossments 8 are relatively wide, the needles will tend to spring back from their flat position.

Spring back is more pronounced by needles of smaller radius. This condition may be minimized by tapering the embossments, as indicated by 14 in FIG. 2A.

As indicated in FIG. 2, the embossments 8 are consecutively numbered so that the needles, when inserted, are readily counted. The embossments are preferably spaced so that the needles do not overlap, or any overlapping is minimal. While semicircular needles are shown, straight needles may be inserted. In practice, however, semicircular needles are used in greater quantity than straight needles.

When the needle count, following surgery, is completed, the collector units are folded into mutual contact, as shown in FIGS. 3 and 4, that is, the undepressed areas are in mutual engagement. This includes the peripheral frames 7. In the structure illustrated, the two units are held in mutual engagement by a pair of magnet strips 5, however, other conventional means for joining the collector units may be used.

If desired, the depressed areas 6 may be enlarged to provide flat magnet strip 9 to receive flat surgical blades (not shown).

The depressed portions 6 may be formed by heat and pressure which increases the density of the depressed portions and provides a smooth surface.

Referring to FIGS. 5 through 8, a second embodiment of the collector is shown having a pair of implement collector units 10. Each unit 10 has a relatively rigid backing plate 12 which is covered by a soft porous foam pad 14. The plates 12 may be composed of any material which provides support to the pads 14, such as plastic, cardboard, or the like. The pads 14 are composed of a foamable polymer, such as polyurethane, which produces a porous soft surface. The backing plates 12 are articulately connected by a dual hinge 16 formed by weakening the plates 12 along parallel lines.

Magnet strips 18 are mounted along the margin of each pad 14 to be in mutual contact when the units 10 are folded. Thus, the strips 18 hold the pads 14 together when mutually engaged. Each pad 14 is bordered by a peripheral frame 20. A magnet strip 19 of larger size than the strips 18 may be positioned on the backing strips 12 to receive flat surgical implements, such as blades. The strip 19 is of a height below the peripheral frame 20 to prevent any interference with the mutual engagement of the peripheral frames 20 when the units 10 are folded.

Located interior of the peripheral frames 20 are rows and columns of needle receiving embossments 22. As most clearly shown in FIG. 8, the embossments 22 taper from a relatively wide portion 21 to a relatively narrow portion 23. Advantageously, the embossments 22 are sequentially numbered so that retained needles can be readily counted.

Surrounding each embossment 22 are crescent-shaped depressions 24. Each depression 24 is formed by a pair of articulately-shaped recesses 26 which extend laterally outward in an arc from each embossment 22 in opposite directions. As shown most clearly in FIGS. 5 and 7, the recesses 26 have a relatively flat portion 28 which extends in an arc outward from the embossment 22. The flat portions 28 represent the deepest portion of the depressions 24.

Referring to FIGS. 5 and 6, the column of crescent-shaped depressions 24 are formed by a series of crests 30 which angle downward in a sloping area 32 to the flat portions 28 and embossments 22. The embossments 22 longitudinally extend from the crest 30 of an adjacent depression 24 to the sloping area 32. The crests 30 form a shoulder 34 with the flat portions 28.

The formation of the crescent depressions 24 by means of the series of crests 30 which slope downward to the flat portions 28 allows a maximum number of depressions 24 to be placed on the pads 14 while keeping adjacent retained needles spaced from one another. Thus, desirably the needles which are retained on the pads 14 should not touch or in any way interfere with each other. To accomplish this with depressions of a single depth, and in one plane, would require significantly more spacing between adjacent depressions.

As shown in FIG. 8, when the needles N1,N2 are placed through the embossments 22, each end rests upon the sloping area 32. The retained needles N1,N2 are therefore oriented in a slightly angular configuration. In this configuration, the needles N1,N2 require less longitudinal space than if flat. When an entire column of depressions 24 is filled, the needles form a stack of slightly angularly oriented needles which do not touch one another.

The arcuate shape of the recesses 26 complements the arcuate shape of curved needles which are most often employed in surgical operations. Thus, as shown in FIG. 8, the needles N1,N2 nest within the recesses 26. The flat portion 28, the sloping area 32, and the shoulder 34 form a contoured pocket to help retain the needles. Thus, the crescent depressions 24 held prevent the needles from being detached from the embossments 22.

The taper of the embossments 22 is also important. Referring to FIG. 8, the small needle, N2, is shown extending through the narrower portion 23 of the embossment 22. Conversely, the large needle, N1, is shown extending through the wider portion 21 of the embossment 22. In both cases, the needles, N1 and N2, are lying essentially flat against the pad 14. The taper is important for two reasons. First, large needles, such as N1, require a larger embossment to prevent them from ripping the embossment and becoming detached. However, if the width of the embossment is significantly larger than the diameter of the needle, the needle will have a tendency to spring back to the upright position in which it was inserted. This is not desirable since the needle is more apt to cut operating room personnel when the units 10 are unfolded, and are also more apt to pierce through the backing plates 12 when the units 10 are folded. Thus, the taper allows the operator to insert a particular needle through the embossment 22 at a point of proper width to ensure that the needle will remain flat.

It should be understood that the columns of crescent-shaped depressions 24, including the crests 30, are depressed with respect to the peripheral frames 20. Thus, when the units are folded, the peripheral frames 20 mutually engage and completely encase the depressions 24.

Referring to FIGS. 9 through 11, a third embodiment of the collector will now be described. The collector has a pair of collector units 36 which each have a relatively rigid backing plate 38. The plates 38 are covered with a plastic sheet 40. The sheet 40 is preferably formed of a semi-rigid elastomer, such as styrene, which is relatively impervious to penetration by a surgical needle. The units 36 are articulately connected along a hinge line 42. Any suitable means may be employed to allow the units 36 to pivot with respect to each other. The sheet 40 is bordered by a peripheral frame 44. Located interior of the frame 44 are rows and columns of crescent-shaped depressions 46. Advantageously, the depressions 46 may be sequentially numbered to provide a means for counting used needles.

A series of elongate bar magnets 48, 50, 52, and 54 are sandwiched between the backing plate 38 and the sheet 40. The magnet 48 is located along one margin of each sheet 40. When the units 36 are folded, the magnets 48 mutually engage to hold the units 36 together. The magnets 50,54 run longitudinally essentially beneath the central portion of each depression 46. The magnets 50,54 magnetically attract and hold the needles within the depressions 46. The magnet 52 runs longitudinally between the two columns of depressions 46, and may be used to magnetically hold flat surgical instruments, such as blades.

In one embodiment, longitudinal grooves are formed in the underside of the sheet 40. The magnets 48, 50, 52, and 54 are then adhesively bonded in the grooves. To complete the unit 36, the backing strip 38 is laminated to the underside of the magnets 48, 50, 52, and 54. It should be understood that due to the contour and depth of the depressions 46, the grooves for the magnets 50,54 will be most prominent at the deepest portion of the depression 46. The sectional view of FIG. 10 is taken generally through this area. Thus, in FIG. 10, the magnet 50 is shown embedded within a groove 56.

The magnets 48, 50, 52, and 54 may be affixed to the sheet 40 through another process. In this process, the sheet 40 is vacuum formed around the magnets 48, 50, 52, and 54, thereby locking the styrene sheet 40 and magnets 48, 50, 52, and 54 to each other.

Each depression 46 has a pair of arcuately-shaped recesses 60 which extend laterally outward in an arc and in opposite directions from the magnets 50,54. The recesses 60 are the deepest portion of the depressions 46. The depressions 46 are formed by crests 62 which slope downward in an area 64. At the extremities of the depressions 46, the sloping area 64 extends down to the recesses 60. However, in the central portion of each depression 46, beneath which the magnets 50,54 lie, the sloping area 64 extends down until it interfaces with the magnets 50,54 along a line 65.

As most clearly shown in FIG. 10, the magnets 50,54 are upraised with respect to the recesses 60. The surface 40 in each depression 46 has a needle area 68 which lies above the magnets 50,54 and which extends from the line 65 to the shoulder 66.

In order to retain a surgical needle, it is preferable that the needle be placed on the area 68. This is true, because a needle will nest within the depression 46 when on the area 68. As similarly discussed above with respect to the second embodiment, the arcuate nature and depth of the depression is important. The arcuate shoulder 66 and recesses 60 conform to an arcuate needle. Thus, a pocket is formed by the sloping area 64, the recesses 60, and the shoulder 66 which acts to hold the needles.

In FIG. 9, a needle N3 is shown retained on the area 68. The needle N3 is confined on one longitudinal side by the shoulder 66, and on the other longitudinal side by the upwardly sloping area 64. Thus, the needle is securely retained.

The unique structure of the depressions 46 acts to ensure that the needle N3 will be drawn to and retained on the area 68, even if the needle is not placed by the operator on the area 68. Thus, if a needle is placed in the position shown in phantom in FIG. 9, it is drawn down the sloping area 64 toward the shoulder 66 onto the area 68. This phenomenon is due, in part, to at least four factors. First, since the sloping area 64 slopes downward, gravity tends to pull the needles downward. Secondly, as best shown in FIG. 11, the magnet 54 is closest to the surface 40 in the area 68. There is a space between the magnet 54 and the crest 62. Thus, the magnetic attraction will be greatest at the area 68 which will tend to pull the needles. Thirdly, the sides of the magnets 50,54, as well as their top surfaces, are "exposed" beneath the surface 40 in the area 68. As a result, the magnetic attraction in the area 68 is even greater due to the greater magnetic surface area exposed. Fourthly, when the central area of larger needles is positioned around the line 65, portions on the ends of the needles do not touch the surface 40. This reduces frictional forces and makes it easier for the magnets 50,54 to pull the needle toward the area 68.

As similarly discussed above with respect to the second embodiment, the contour of the depressions 46 allows many more depressions to be placed on the surface 40. Moreover, the columns of crescent depressions 46 including the crests 62 are depressed with respect to the peripheral frames 44. Thus, when the units 36 are folded, the peripheral frames 44 mutually engage and completely encase the depressions 46.

It should be understood that the third embodiment may be modified so that the sheet 40 is made of a soft porous foam, such as a urethane, instead of a semirigid plastic, such as styrene. The needles, as in the second embodiment, would be magnetically held within the depressions 46. However, if desired, the needles could be inserted in the shoulder 66 above the magnets 50,54 to provide a further means to hold the needles within the depressions 46.

I claim:
1. A collector for surgical needles comprising:
   (a) a collector unit;
   (b) a plurality of depressions in said unit, each of said depressions being formed by an inclined ramp surface which slopes downward from a crest into a recess, adjacent crest and recesses forming a shoulder, each of said ramp surfaces being generally parallel to, but offset from the adjacent ramp surfaces, said recess being of a shape and depth to permit a surgical needle to nest within said recess and to lie along said ramp surface, said shoulder and crest being adapted to confine said needles within the recess.

2. The collector of claim 1 further comprising an embossment positioned within said depressions, said embossment being penetrable by said needles to hold said needles in said depressions.

3. The collector of claim 1 further comprising a magnetic area located within said depressions, said area being adapted to draw a surgical needle down into said depression to securely hold said needles.

4. The collector of claim 2 wherein said embossment has a narrower portion for receiving smaller diameter needles and a wider portion for receiving larger diameter needles, said portions deflecting said needles into an essentially flat position on said unit.

5. The collector of claim 1 wherein said unit is composed of a material essentially impervious to penetration by a surgical needle.

6. The collector of claim 1 wherein said unit is composed of a soft porous foam.

7. A collector for surgical needles comprising:
(a) a collector unit;
(b) a plurality of needle receiving elements spaceably located on said unit; and
(c) a plurality of crescent-shaped recesses extending outward in an arc in opposite directions from said receiving element, each of said depressions being formed by a crest which slopes downward into said recesses, adjacent crests and recesses forming a shoulder, said recess being of a shape and depth to receive a curved surgical needles, said shoulder and crest being adapted to confine said needles within the recess.

8. The collector of claim 7 further comprising a cover articulately connected to said unit.

9. A collector for surgical needles comprising:
a top having a central portion and a peripheral portion;
a bottom having a central portion and a peripheral portion;
said top and bottom being articulately connected and movable between an essentially coplanar needle-receiving position and a folded position;
a means for joining the top and bottom when in a folded position;
a needle collector unit disposed between said top and bottom when in a folded position, said collector unit having a central portion adapted to receive surgical needles and an upstanding peripheral frame portion surrounding the needle-receiving central portion, said peripheral frame portion having a height such that the peripheral portion of said collector top or collector bottom mutually engage said peripheral frame portion of said collector unit to form an enclosure around the needle-receiving central portion when the collector is in a folded position;
a plurality of transversely penetrable needle-receiving embossments spaceably mounted on said central portion of the collector unit; and
an area of depression extending laterally outward from each of said needle-receiving embossments in opposite directions, said area being a complementary shape to a surgical needle such that said narrow and wider portions of said needle-receiving embossments deflect said needles into essentially flat positions nested within said depression when inserted therethrough;
said areas of depression further comprising a bottom portion, a top portion, and a sloping portion depending from said top portion to said bottom portion to provide a contoured pocket; said top, bottom, and sloping portions each being depressed lower than said peripheral frame such that the peripheral frame and collector top mutually engage to completely encase the depressions.

10. The collector of claim 9 having a pair of collector units.

11. The collector of claim 9 wherein said needle-receiving embossments have a narrow portion for receiving smaller needles and a longitudinally spaced wider portion for receiving larger needles.

12. The collector of claim 11 having a pair of collector units.

* * * * *